US012133767B2

United States Patent
Duplat et al.

(10) Patent No.: US 12,133,767 B2
(45) Date of Patent: Nov. 5, 2024

(54) SYSTEM AND METHOD FOR REAL-TIME LOCALIZATION

(71) Applicants: ROBEAUTE, Paris (FR); SORBONNE UNIVERSITÉ, Paris (FR); CENTRE NATIONAL DE LA RECHERCHE SCIENTIFIQUE, Paris (FR)

(72) Inventors: Bertrand Duplat, Paris (FR); Quentin Francois, Paris (FR); Sinan Haliyo, Paris (FR); Régis Marchiano, La Frette-sur-Seine (FR); Stéphane Regnier, Bois-Colombes (FR)

(73) Assignees: ROBEAUTE, Paris (FR); SORBONNE UNIVERSITÉ, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 191 days.

(21) Appl. No.: 17/293,681

(22) PCT Filed: Nov. 14, 2019

(86) PCT No.: PCT/EP2019/081344
§ 371 (c)(1),
(2) Date: May 13, 2021

(87) PCT Pub. No.: WO2020/135945
PCT Pub. Date: Jul. 2, 2020

(65) Prior Publication Data
US 2022/0000454 A1   Jan. 6, 2022

(30) Foreign Application Priority Data

Nov. 14, 2018 (EP) .................................. 18206245

(51) Int. Cl.
*A61B 8/08* (2006.01)
*A61B 8/00* (2006.01)
*A61B 34/30* (2016.01)
*G06T 7/00* (2017.01)
*G06T 7/30* (2017.01)

(52) U.S. Cl.
CPC ............ *A61B 8/481* (2013.01); *A61B 8/4477* (2013.01); *A61B 34/30* (2016.02); *G06T 7/0014* (2013.01);
(Continued)

(58) Field of Classification Search
CPC .................. A61B 8/481; A61B 8/0808; A61B 2034/2063; G06T 7/0014; G06T 7/30; G06T 2207/30016
See application file for complete search history.

(56) References Cited

U.S. PATENT DOCUMENTS 5,605,673 A * 2/1997 Schutt .................. A61K 49/227
424/9.51
2012/0035434 A1* 2/2012 Ferren .................. A61B 5/4839
600/301
(Continued)

FOREIGN PATENT DOCUMENTS

WO   2010/052494 A1   5/2010
WO   2012/172458 A1   12/2012
(Continued)

OTHER PUBLICATIONS

International Search Report and Written Opinion issued on Jan. 31, 2020 in corresponding International Application No. PCT/EP2019/081344; 10 pages.
(Continued)

*Primary Examiner* — Boniface N Nganga
(74) *Attorney, Agent, or Firm* — Maier & Maier, PLLC

(57) ABSTRACT

This system for real-time localization of a millimetric or submillimetric object, such as a microrobot, in a viscoelastic medium, in particular in an organ of a subject such as a brain, a liver or a pancreas, includes: at least one bubble configured to be attached to said object, the or each bubble having a hermetic envelope filled with a gas; at least one
(Continued)

ultrasound transducer configured to emit initial ultrasound signals and to detect deflected ultrasound signals deflected at the surface of the bubble(s); a processing unit in communication with the ultrasound transducers and configured to generate localization data of the object from localization data of the bubble(s) based on the deflected ultrasound signals detected by the ultrasound transducers.

20 Claims, 2 Drawing Sheets

(52) U.S. Cl.
CPC ...... *G06T 7/30* (2017.01); *G06T 2207/30016* (2013.01)

(56) References Cited

U.S. PATENT DOCUMENTS

2016/0106395 A1* 4/2016 Hynynen ................ A61B 8/54
600/431

2019/0076112 A1* 3/2019 Montgomery, Jr. ..... A61B 8/12

FOREIGN PATENT DOCUMENTS

| WO | WO-2018112664 A1 * | 6/2018 | ............ A61B 34/10 |
| WO | WO-2019213389 A1 * | 11/2019 | ............ A61B 34/20 |

OTHER PUBLICATIONS

Chengcheng Niu et al., "Poly(Lactide-Co-Glycolide) Ultrasonographic Microbubbles Carrying Sudan Black for Preoperative and Intraoperative Localization of Lymph Nodes", Clinical Breast Cancer, vol. 12, No. 3, Jun. 1, 2012; pp. 199-206.

Kirsten Christensen-Jeffries et al., "Microbubble Axial Localization Errors in Ultrasound Super-Resolution Imaging", IEEE Transactions On Ultrasonics, Ferroelectrics and Frequency Control, vol. 64, No. 11, Nov. 1, 2017; pp. 1644-1654.

A. R. Sever et al., "Sentinel node identification using microbubbles and contrast-enhanced ultrasonography", Clinical Radiology, vol. 67, No. 7, Jul. 1, 2012; pp. 687-694.

* cited by examiner

SYSTEM AND METHOD FOR REAL-TIME LOCALIZATION

FIELD

The present invention relates to a system and a method for real-time localization of a millimetric or submillimetric object in a viscoelastic medium, in particular in an organ of a subject such as a brain, a liver or a pancreas.

BACKGROUND

The ability to reach deep and functional structures without damage is a major challenge in mini-invasive surgery, especially in neurosurgery. Thanks to microtechnologies, it becomes possible to send a fully autonomous micromedical device inside an organ of a subject, such as a brain, a liver or a pancreas. However, to ensure reliability, such a micromedical device requires a localization system with a position accuracy at least equal to the size of the device, even in a heterogeneous and sensitive organ.

Existing localization systems do not meet all the requirements of position accuracy, depth, mini-invasiveness, and innocuity for the subject. In particular, some nuclear medicine techniques make it possible to localize in real time a submillimetric object in an organ, however such techniques generate radiation that is dangerous for the subject beyond a certain dose of exposure. Therefore, such techniques cannot be used for a long time on the same subject. In practice, real-time localization during an operation is performed by exploiting the part of the surgical instruments that is outside the body when there is one. However, the miniaturization of surgical instruments and the transition to fully immersed instruments make this technique unusable.

It is these drawbacks that the invention is intended more particularly to remedy by proposing a system and a method for real-time localization of a millimetric or submillimetric object in a viscoelastic medium, in particular in an organ of a subject such as a brain, a liver or a pancreas, which enable reliable localization, with high position accuracy, high depth, limited invasiveness, and without risk for the subject.

SUMMARY

For this purpose, a subject of the invention is a system for real-time localization of a millimetric or submillimetric object, such as a microrobot, in a viscoelastic medium, in particular in an organ of a subject such as a brain, a liver or a pancreas, said system comprising:
  at least one bubble configured to be attached to said object, the or each bubble comprising a hermetic envelope filled with a gas;
  at least one ultrasound transducer configured to emit initial ultrasound signals and to detect deflected ultrasound signals deflected at the surface of the bubble(s);
  a processing unit in communication with the ultrasound transducer and configured to generate localization data of the object from localization data of the bubble(s) based on the deflected ultrasound signals detected by the ultrasound transducer.

Within the frame of the invention, an ultrasound signal deflected at the surface of a bubble is an ultrasound signal which is reflected, refracted and/or scattered at the surface of the bubble. The bubble being hermetic and attached to the object, it can not burst with air escaping from the inside such as in cavitation cavitation processes where burst generated ultrasound is monitored.

According to one embodiment, the deflected ultrasound signal is an ultrasound signal reflected at the surface of the bubble, either in a specular manner or in a diffuse manner. When the reflection is specular, the deflected ultrasound signal may be detected by the ultrasound transducer which has emitted the initial ultrasound signal. When the reflection is diffuse, the deflected ultrasound signal may be detected by another ultrasound transducer than the one which has emitted the initial ultrasound signal.

According to one embodiment, the deflected ultrasound signal is an ultrasound signal refracted at the surface of the bubble. Then, the deflected ultrasound signal may be an ultrasound signal transmitted through the bubble and detected by another ultrasound transducer than the one which has emitted the initial ultrasound signal.

The reflection of an ultrasound signal at an interface is directly dependent on the acoustic impedance difference at the interface. The reflection may be specular or diffuse, depending on the ratio between the size of the interface irregularities and the wavelength.

According to one embodiment, at least part of the deflection of the initial ultrasound signal is a reflection occurring at the interface between the viscoelastic medium and the envelope of the bubble.

According to one embodiment, the main part of the deflection of the initial ultrasound signal is a reflection occurring at the interface between the viscoelastic medium and the envelope of the bubble.

According to one embodiment, at least part of the deflection of the initial ultrasound signal is a reflection occurring at the interface between the envelope of the bubble and the gas of the bubble.

Advantageously, the thickness of the envelope of the bubble is less than 100 μm, preferably less than 50 μm, preferably less than 20 μm, so that the reflected signals at the two interfaces, i.e. the interface between the viscoelastic medium and the envelope of the bubble, on the one hand, and the interface between the envelope of the bubble and the gas of the bubble, on the other hand, have a spatial shift of less than the expected resolution for the localization.

The system for real-time localization according to the invention is based on the acoustic resonance of the bubble(s) in the viscoelastic medium. When studying the propagation of a wave in a heterogeneous medium having a matrix in which diffusers are distributed, it can generally be considered that, if the wavelength is large compared to the size of the diffusers, the propagation of the wave is little or not changed by their presence. However, in the case where the diffusers are resonant bubbles, their presence greatly modifies the propagation of the wave.

The motion of a bubble receiving ultrasound signals can be described by a harmonic oscillator model, the resonance frequency of the system being $\sqrt{k/m}$, where the mass m corresponds to the mass of the viscoelastic medium displaced by the presence of the bubble and the stiffness k corresponds to the internal pressure force allowing the bubble to be in equilibrium, which is linked to the compressibility of the gas of the bubble. Because the two parameters of the oscillator are given by two different fluids, i.e. the viscoelastic medium and the gas of the bubble, it is possible to have a resonance at wavelengths very large compared to the size of the bubble.

In this way, thanks to the invention, it is possible to reliably localize a millimetric or submillimetric object linked to the bubble. In particular, the localization system according to the invention is capable of determining a position, orientation, or both, of the millimetric or submillimetric object.

According to an advantageous feature, the or each ultrasound transducer is configured to emit initial ultrasound signals at a frequency of the order of a resonance frequency of the bubble. For frequencies of the order of the resonance frequency of the bubble, the wavelength in the viscoelastic medium is very large compared to the radius of the bubble, allowing to consider that, at these frequencies, only the radial vibration modes of the system are excited by an acoustic wave. Moreover, at these frequencies, the wavelength in the gas of the bubble is also very large compared to the radius of the bubble, implying that the gas of the bubble undergoes uniform compressions and depressions and that only one degree of freedom can be considered for the bubble.

In one embodiment, the envelope of the bubble is made of a polymer, for example a UV-curable hybrid inorganic-organic polymer such as ORMOCLEAR manufactured by the company MICRO RESIST TECHNOLOGY GmbH, and the gas of the bubble is air. Advantageously, the envelope of the bubble has properties adapted to allow deformation of the bubble under the effect of ultrasound signals. The air within the envelope is thus encapsulated so as to avoid bubble bursting, said bursting being what is targeted for example in cavitation processes where generated ultrasound is tracked.

According to one embodiment, the frequency of the emitted initial ultrasound signals is lower than or equal to 10 MHz, preferably lower than or equal to 8 MHz, more preferably lower than or equal to 2 MHz. The two major sources of attenuation of a sound wave in a body of a subject are absorption inside tissues and reflections at interfaces. The absorption being a linear function of the sound wave frequency and the travelled path, it is desirable to keep the frequency of the emitted initial ultrasound signals as low as possible.

According to one embodiment, the localization system comprises at least three ultrasound transducers configured to emit initial ultrasound signals and to detect deflected ultrasound signals deflected at the surface of the bubble(s).

In one embodiment, the processing unit of the localization system comprises a trilateration module configured to determine a spatial position and/or orientation of the object from a distance between each ultrasound transducer and the bubble(s). In the case of the determination of the orientation of the object, at least two bubbles attached to the object are required, and for each bubble a distance between each ultrasound transducer and the bubble is determined. Trilateration is the process of determining the absolute or relative location of a point in space by measurement of distances, using the geometry of circles, spheres or triangles. In contrast to triangulation, it does not involve the measurement of angles, although triangulation techniques may also be employed. It is understood that, within the frame of the invention, the term "trilateration" refers to trilateration or triangulation.

In particular embodiments of the invention, the distance between each ultrasound transducer and the bubble(s) may be calculated based on a time delay between the emission of an initial ultrasound signal and the detection of the deflected ultrasound signal and/or based on an attenuation equation in the viscoelastic medium.

According to one feature of the invention, the processing unit of the localization system is configured to communicate with the ultrasound transducers and to cause each of the ultrasound transducers to emit initial ultrasound signals in a sequential manner. In this way, interferences between ultrasound signals are avoided temporally. In particular, in one embodiment, each ultrasound transducer emits ultrasound pulses.

According to one feature, the or each bubble has a diameter comprised between 20 μm and 1 mm. In one embodiment, the diameter of the bubble is of the order of a characteristic dimension of the object to which it is attached. Above 20 μm, the bubble would not be stable without a hermetic, stable envelope. It would collapse.

According to one embodiment, the or each bubble is configured to be structurally anchored on the object. For example, the bubble may be positioned in a cage structure being part of the object.

According to another embodiment, the bubble is assembled with the object by means of at least one fastening element, such as an adhesive layer.

According to one embodiment, the localization system comprises at least two distinct bubbles configured to be attached to the object, such that both a position and an orientation of the object can be determined. According to an advantageous embodiment, the localization system comprises three bubbles configured to be distributed on the object without being aligned. Such an arrangement facilitates the recognition of an orientation of the object. Advantageously, the localization system comprises three bubbles arranged at 90° relative to one another on the object.

According to one embodiment, the localization system comprises a registration module configured to match the coordinates of each point of the localization data generated by the processing unit with the coordinates of corresponding images on a reference image obtained with a medical imaging system, using image registration algorithms. This makes it possible to display the position and orientation of the object in an anatomical image, such as an image obtained from a magnetic resonance imaging (MRI) system, a fluoroscopy system, a computed tomography (CT) system, an ultrasound system or other system.

According to one embodiment, the processing unit is configured to use super-resolution processing to localize an object smaller than the wavelength of the emitted initial ultrasound signals. In super-resolution processing, it is considered that there is only one object to locate and that its strongest returned signal is located at the center of the spatial width of the returned signal. For example, if a 3-mm width signal returns to the sensor, it can be considered, even if the object has a dimension of 500 μm, that it is at the center of the signal width. This makes it possible to locate small objects with less accurate systems.

Thanks to super-resolution processing, longer wavelengths corresponding to lower frequencies can be used, resulting in reduced attenuation of the ultrasound signals by the tissues of the subject and making it possible to reach greater depth and/or to cross thicker layers and therefore reduce the invasiveness.

According to one feature, the processing unit is configured to generate localization data based on the deflected ultrasound signals detected by the ultrasound transducers and the physical properties of the surrounding of the object. The integration of the physical properties of the surrounding of the object improves the registration with an anatomical image, such as an image obtained from a magnetic resonance imaging (MRI) system, a fluoroscopy system, a computed tomography (CT) system, an ultrasound system or other system.

According to one feature, the localization system comprises more than three ultrasound transducers. A high number of ultrasound transducers advantageously improves the measurement accuracy.

According to one embodiment, each ultrasound transducer is configured to be fixed on the outside of a body part of a subject, e.g. on the outside of the skull of a subject or on the outside of the abdomen of a subject. Advantageously, the ultrasound transducers are precisely positioned relative to one another. In particular, a headgear or a belt may be used to support the ultrasound transducers so that they are precisely pre-positioned.

According to one embodiment, each ultrasound transducer is configured to be positioned in a hole made in the outer layers of a body part of a subject, e.g. in the outer layers of the skull of a subject or in the outer layers of the abdomen of a subject. In this way, movement between the body part and the ultrasound transducer is prevented. In one embodiment, the hole in the outer layers of the skull is arranged in the outer table and in the diploë (or spongy cancellous bone).

According to one embodiment, the object to be localized is a microrobot having a propellant structure in high viscosity materials, such as the viscoelastic materials of the brain, the liver or the pancreas. By microrobot, it is meant a robot having a size of less than one millimeter, or a tenth of a millimeter. Such a microrobot is adapted for medical applications, and in particular to move inside organs of a subject, especially inside the brain, the liver or the pancreas of a subject. The microrobot can reach deep regions of an organ such as the brain while limiting damages to cell structures upon its entry and passage through the organ.

Another subject of the invention is a method for real-time localization of a millimetric or submillimetric object, such as a microrobot, in a viscoelastic medium, in particular in an organ of a subject such as a brain, a liver or a pancreas, wherein at least one bubble is configured to be attached to said object, the or each bubble comprising a hermetic envelope filled with a gas, the method comprising steps of:
- by means of at least one ultrasound transducer, producing emitted initial ultrasound signals at a given frequency and detecting deflected ultrasound signals deflected at the surface of the bubble(s);
- generating localization data of the object from localization data of the bubble(s) based on the deflected ultrasound signals detected by the or each ultrasound transducer.

Advantageously, the given frequency is selected so as to be of the order of a resonance frequency of the bubble.

According to one embodiment, the method uses at least three ultrasound transducers and comprises steps of:
- producing emitted initial ultrasound pulses by means of the at least three ultrasound transducers in a sequential manner and detecting deflected ultrasound signals deflected at the surface of the bubble by means of the at least three ultrasound transducers;
- generating localization data of the object from localization data of the bubble(s) based on the deflected ultrasound signals detected by the at least three ultrasound transducers.

According to one embodiment, the step of generating localization data based on the deflected ultrasound signals comprises a step of calculating the distance between the bubble and each ultrasound transducer. In a first implementation, the distance between the bubble and each ultrasound transducer is calculated based on a time delay between the emission of an initial ultrasound signal and the detection of the ultrasound signal deflected at the surface of the bubble. In a variant, which may be implemented alone or in combination with the first implementation, the distance between the bubble and each ultrasound transducer is calculated based on the intensity of the deflected ultrasound signal detected by the ultrasound transducer and an attenuation equation in the viscoelastic medium. Then, the position of the bubble can be determined from the distance between the bubble and each ultrasound transducer by any suitable method, e.g. by means of a trilateration method.

According to one embodiment, prior to the step of producing and detecting ultrasound signals by means of the ultrasound transducer(s), the method comprises a step of positioning the or each ultrasound transducer on a body part of a subject in the vicinity of an organ, such as a brain, a liver or a pancreas, in which the object is to be localized. In particular, the or each ultrasound transducer may be fixed on the outside of a body part of a subject such as the head or the abdomen, e.g. by means of a support such as a headgear or a belt. As a variant, the or each ultrasound transducer may be positioned in a hole made in the outer layers of a body part of a subject.

According to one embodiment, prior to the step of producing and detecting ultrasound signals by means of the ultrasound transducer(s), the method comprises a step of introducing the object, with the bubble(s) attached to it, in an organ of a subject, such as a brain, a liver or a pancreas, e.g. by means of a surgical needle.

The invention also relates to a computer program comprising instructions for the implementation of the calculation steps of the method described above when the program is executed by a computer.

The invention also relates to a non-transitory computer readable medium comprising instructions for the implementation of the calculation steps of the method described above when the instructions are executed by a computer.

BRIEF DESCRIPTION OF THE DRAWINGS

Features and advantages of the invention will become apparent from the following description of an embodiment of a system and a method for real-time localization according to the invention, this description being given merely by way of example and with reference to the appended drawings in which.

In the invention, the expression hermetic envelop means that the bubble is airtight and the wall is configured not to explode under ultrasound pressure such as in cavitation. For the tracking of the bubble to be carried out, said bubble must remain attached to the object of the invention.

DETAILED DESCRIPTION

Figure 1:
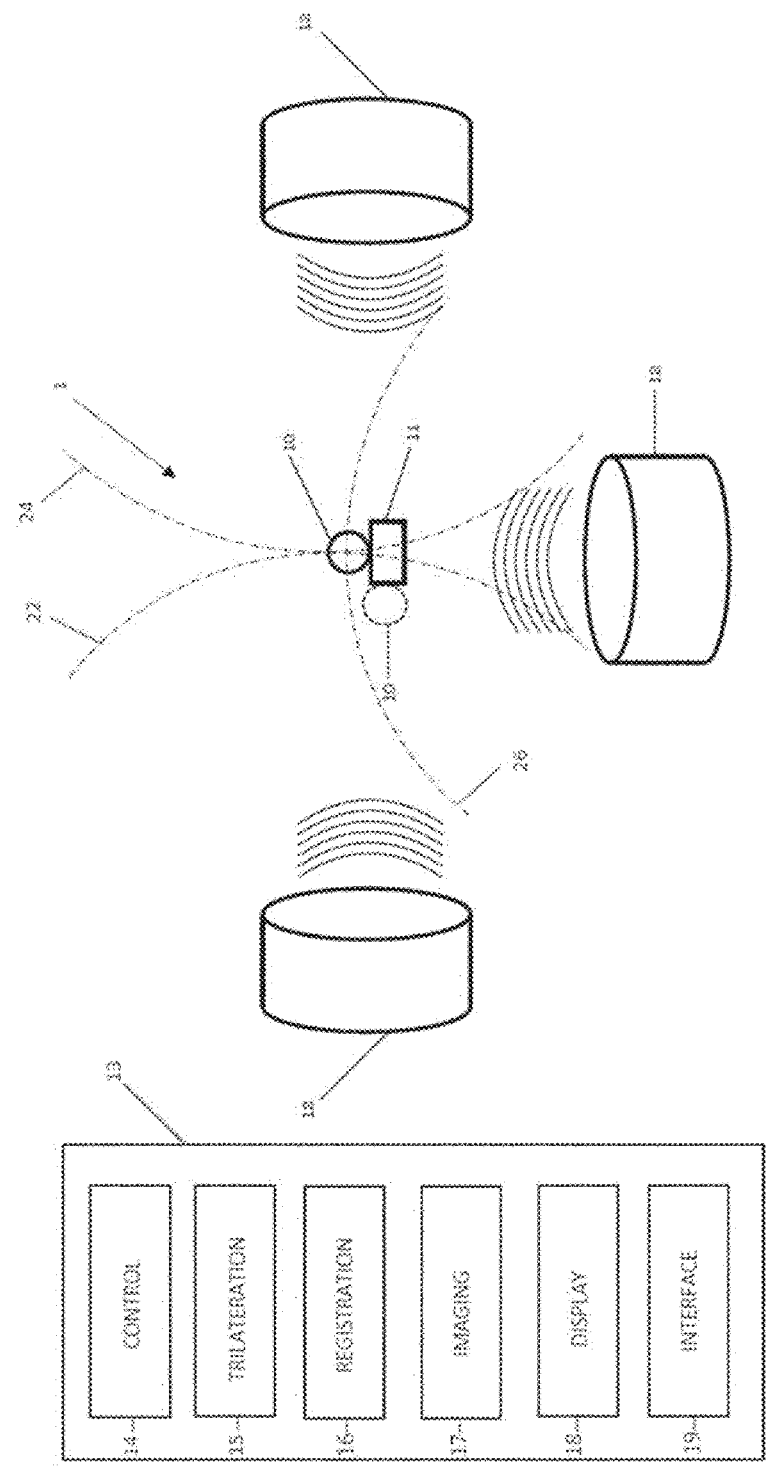
FIG. 1 is a schematic view of a localization system according to an embodiment of the invention for real-time localization of a microrobot.
Figure 2:
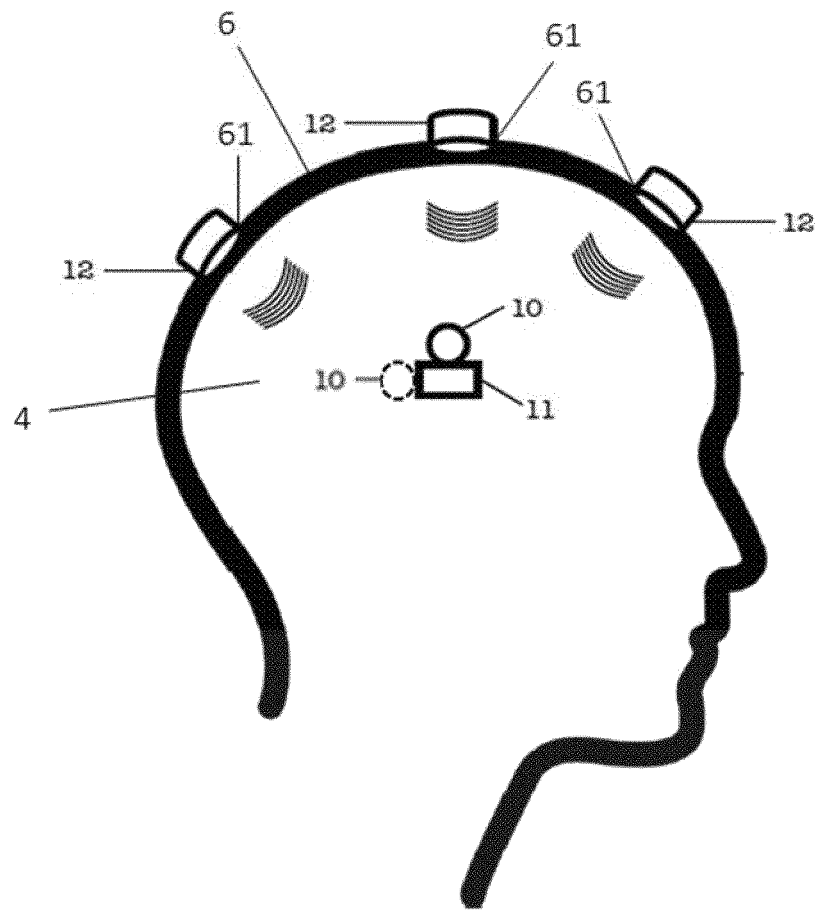
FIG. 2 is a schematic view of elements of the localization system of FIG. 1 arranged for real-time localization of a microrobot in the brain of a subject.

According to the illustrative embodiment shown in FIGS. 1 and 2, a microrobot 11 is intended to be introduced and localized in real-time in the brain 4 of a subject. The microrobot 11, having a size of less than one millimeter, is for example configured to perform therapeutic or surgical actions in the brain 4 of the subject while being controlled by a neurosurgeon. The microrobot 11 has a propellant structure ensuring that it can reach deep regions of the brain 4 while limiting damages to cell structures. The position, orientation, or both, of the microrobot 11 in the brain 4 may be accurately identified using an ultrasound-based localization system 1 according to the invention, as shown in the figures.

In the example shown in FIGS. 1 and 2, the localization system 1 comprises two bubbles 10 attached to the microrobot 11, one being shown in dotted lines, it being understood that only one bubble 10 may be used to determine the position of the microrobot, whereas two or more bubbles make it possible to determine, in addition to the position, the orientation of the microrobot.

By way of a non-limiting example, each bubble 10 has a diameter of 160 µm; the envelope of each bubble 10 is 26 µm thick and made of UV-curable hybrid inorganic-organic polymer ORMOCLEAR; the gas of each bubble 10 is air; each bubble 10 is attached to the microrobot 11 by means of an adhesive layer.

The localization system 1 also comprises three ultrasound transducers 12, each intended to be placed in a hole 61 made in the outer layers of the skull 6 of the subject, i.e. the outer table and the diploë (or spongy cancellous bone). The ultrasound transducers 12 are configured to emit initial ultrasound signals and to detect deflected ultrasound signals deflected at the surface of the bubbles 10.

In the illustrated example, the frequency of the ultrasound signals emitted by each of the three ultrasound transducers 12 is targeted at 2 MHz, which is aimed to correspond to a resonance frequency of each bubble 10 located in the viscoelastic medium formed by the brain 4. In these conditions, it can be considered that only the radial vibration modes of the system are excited. Then, the deflected ultrasound signals mainly are ultrasound signals reflected at the surface of the bubble 10 in a specular manner, which may be detected by the ultrasound transducer 12 which has emitted the initial ultrasound signal.

It is noted that, in other embodiments of the invention, the frequency of the ultrasound signals emitted by the ultrasound transducers 12 can be lowered in order to limit the attenuation of the ultrasound signals in the head of the subject and thus increase the accuracy. Then, the structure if each bubble 10 is advantageously adapted so that a resonance frequency of the bubble 10 substantially corresponds to the lowered signal frequency.

Within the localization system 1, the ultrasound transducers 12 are in communication with a processing unit 13 including a control module 14 configured to cause the ultrasound transducers 12 to emit initial ultrasound pulses in a sequential manner, i.e. one by one. Thanks to the activation of each ultrasound transducer 12 in turn, interferences between ultrasound signals are avoided temporally, ensuring that it is possible to know from which ultrasound transducer 12 an initial ultrasound signal comes from.

The processing unit 13 is generally implemented with one or more hardware processors and a memory. A trilateration module 15 of the processing unit 13 is configured to receive signal data from the ultrasound transducers 12 and process the signal data. In particular, the trilateration module 15 is configured to compute times of flight of ultrasound signals deflected at the surface of the bubbles 10 and received by the ultrasound transducers 12, so as to yield the position of each bubble 10, thus making it possible to determine a position and an orientation of the microrobot 11. It is understood that a plurality of bubbles 10 may be employed on the microrobot 11.

In the illustrated example, the processing unit 13 is further configured to depict the microrobot 11 in medical images. To this end, the processing unit 13 includes a registration module 16 configured to match the coordinates of each point of the localization data generated by the trilateration module 15 with the coordinates of corresponding elements on a reference image obtained with an imaging system 17. In FIG. 1, the imaging system 17 has been shown as part of the processing unit 13 comprising the trilateration module 15 and the registration module 16, but of course it can be physically separated from the processing unit 13 and connected to the registration module 16.

In the example shown in the figures, the processing unit 13 includes a display 18 for viewing anatomical images of the subject obtained with the imaging system 17 and display the position and orientation of the microrobot 11 in the anatomical images. The imaging system 17 may include, e.g., a magnetic resonance imaging (MRI) system, a fluoroscopy system, a computed tomography (CT) system, an ultrasound system or other system. The display 18 also permits a user to interact with the processing unit 13 and its components and functions. This is facilitated by an interface 19, which may include a keyboard, mouse, a joystick or any other peripheral or control to permit user interaction with the processing unit 13.

In an advantageous embodiment, the imaging system 17 is provided to collect real-time intra-operative imaging data. The imaging data may be displayed on display 18. The processing unit 13 may determine the positions of the bubbles 10, and therefore the position and orientation of the microrobot 11, within the real-time images based upon deflected ultrasound signals measured by the ultrasound transducers 12. In particular, this may be obtained by means of a trilateration method as described hereafter, implemented by the trilateration module 15. Of course, within the scope of the invention, other methods than that described below may be used to determine the positions of the bubbles 10.

By way of a non-limiting example, for each bubble 10, the trilateration module 15 is configured to calculate the distance between the bubble 10 and each of the three ultrasound transducers 12 based on a time of flight between the bubble 10 and the ultrasound transducer 12, i.e. the time delay between the emission of an initial ultrasound signal by the ultrasound transducer 12 and the detection of the ultrasound signal deflected at the surface of the bubble 10. The position of the bubble 10 is at an intersection of three spheres 22, 24, 26 each centered respectively on one of the ultrasound transducers 12 and with radii determined by the measured time of flight between the bubble 10 and the ultrasound transducer 12. In FIG. 1, for the clarity of the drawing, the time-of-flight spheres 22, 24, 26 are shown schematically, with the intersection projected in the plane of the figure, only for the bubble 10 in solid lines, it being understood that similar spheres are determined for the bubble 10 in dotted lines.

For each bubble 10, the intersection of the three spheres 22, 24, 26 results in two points, symmetric with respect to the imaged plane, as long as the centers of the three spheres are not aligned with respect to the bubble 10. Thus, the time-of-flight spheres 22, 24, 26 preferably have centers, corresponding to the positions of the ultrasound transducers 12, that are not aligned relative to the bubble 10. However, in case of alignment, beamforming may be employed for the emitted ultrasound signals from one or more of the ultrasound transducers 12 to provide a new origin for the emitted ultrasound signal and eliminate the alignment.

The trilateration yields two positions of the bubble 10, symmetric with respect to the imaged plane. The uncertainty may be broken by means of available information, e.g. by using a priori knowledge, or by slightly moving the ultrasound transducers 12 and observing the relative movement of the bubble 10, getting closer or farther relative to the imaged plane. An additional ultrasound transducer may also be employed on a side of the three ultrasound transducers 12 to break the uncertainty.

Advantageously, the processing unit 13 is configured to use super-resolution processing to localize the bubbles 10, and thus the microrobot 11. Thanks to super-resolution processing, longer wavelengths corresponding to lower frequencies can be used, resulting in reduced attenuation of the ultrasound signals by the tissues of the subject so that greater depth can be reached and thicker layers can be crossed, thus reducing the invasiveness of the localization system and method according to the invention.

A method for real-time localization of the microrobot 11 in the brain 4 of a subject using the localization system 1 comprises the following steps.

First, the three ultrasound transducers 12 are positioned on the skull 6 of the subject, each positioned in a hole 61 in the outer table and the diploe of the skull 6 of the subject. Then, the microrobot 11, with the bubbles 10 attached to it, is introduced into the brain 4 of the subject, e.g. by means of a surgical needle. Then, by activating the control module 14 of the processing unit 13, by means of the interface 19, the three ultrasound transducers 12 are caused to emit initial ultrasound pulses in a sequential manner, one by one, and to detect deflected ultrasound signals deflected at the surface of the bubbles 10.

The trilateration module 15 then automatically generates localization data, based on the deflected ultrasound signals detected by the ultrasound transducers 12, and the registration module 16 matches the coordinates of each point of the localization data generated by the trilateration module 15 with the coordinates of corresponding elements on a reference image obtained with the imaging system 17. The image obtained from the imaging system 17 is displayed on the display 18, together with the position and orientation of the microrobot 11. In this way, the position and orientation of the microrobot 11 in the brain 4 of the subject can be monitored, during its insertion and its displacement in the brain 4 of the subject.

As can be seen from the previous example, a localization system and method according to the invention provide reliable localization of a microrobot or other millimetric or submillimetric object in a viscoelastic medium such as a brain of a subject, with high position accuracy, high depth, limited invasiveness, and without risk for the subject.

The invention is not limited to the examples described and shown.

In particular, in the illustrative embodiment described above, the position of each bubble is determined by calculating the distance between the bubble and each ultrasound transducer based on a time delay between the emission of an initial ultrasound signal and the detection of the ultrasound signal deflected at the surface of the bubble. As a variant, the distance between the bubble and each ultrasound transducer may be calculated based on the intensity of the deflected ultrasound signal detected by the ultrasound transducer and an attenuation equation in the viscoelastic medium, or by any other appropriate method.

According to another variant, the localization system and method of the invention may comprise more than two bubbles attached to the object to be localized. In particular, the use of three bubbles distributed on the object without being aligned, for example arranged at 90° relative to one another on the object, facilitates the recognition of an orientation of the object.

In addition, in the examples above, the localization system and method involve three ultrasound transducers configured to emit initial ultrasound signals and to detect ultrasound signals deflected at the surface of the bubble(s). In other embodiments of the invention, the localization system and method may comprise any number N of ultrasound transducers, with N equal to or higher than 1, the corresponding method for determining the position of the bubble(s) being based on the signals detected by the N ultrasound transducers and information to break potential uncertainty such as a priori knowledge, imposed relative movement, etc.

The invention has also been illustrated in a case where the ultrasound transducers are each positioned in a hole made in the outer layers of the skull. However, in other embodiments, the ultrasound transducers may be fixed in a non-invasive way on the outside of the skull of the subject, or on any other part of the body of the subject close to an organ in which the object is to be localized. The ultrasound transducers may be fixed externally on the body of the subject by any means ensuring that movement between the body and the transducers is prevented, such as for example a headgear in the case of transducers placed on the head of the subject, the localization system and method of the invention thus being minimally invasive.

The localization system and method of the invention can also be applied for real-time localization of a millimetric or submillimetric object in any viscoelastic medium, in particular in a viscoelastic medium other than an organ of a subject, for example in other fields than in the medical field.

The invention claimed is:

1. A system for real-time localization of a millimetric or submillimetric object in a viscoelastic medium based on an acoustic resonance of at least two distinct bubbles in the viscoelastic medium, said system comprising:
   at least two distinct bubbles attached to said object, each bubble comprising a hermetic envelope filled with a gas, each bubble being configured to be either structurally anchored on the object or assembled with the object by means of at least one fastening element;
   at least one ultrasound transducer configured to emit initial ultrasound signals and to detect deflected ultrasound signals deflected at the surface of the at least two distinct bubbles; and
   a processing unit in communication with the ultrasound transducer and configured to generate localization data of the object from localization data of the at least two distinct bubbles based on the deflected ultrasound signals detected by the at least one ultrasound transducer,
   wherein the at least two distinct bubbles are attached to the object in such a way that the localization of the at least two distinct bubbles enable the processing unit to determine a spatial position and an orientation of the object.

2. The system according to claim 1, wherein the at least one ultrasound transducer is configured to emit initial ultrasound signals at a frequency of an order of a resonance frequency of the at least two distinct bubbles.

3. The system according to claim 1, comprising at least three ultrasound transducers configured to emit initial ultrasound signals and to detect deflected ultrasound signals deflected at the surface of the at least two distinct bubbles.

4. The system according to claim 3, wherein the processing unit comprises a trilateration module configured to determine the spatial position and orientation of the object from a distance between each ultrasound transducer and the at least two distinct bubbles.

5. The system according to claim 4, wherein the processing unit is implemented with at least one hardware processors, a memory, and a trilateration module configured to receive signal data from each ultrasound transducer and process the signal data with a trilateration method, the trilateration module being further configured to compute times of flight of ultrasound signals deflected at the surface of the at least two distinct bubbles and received by each ultrasound transducer, so as to yield the position of each bubble in order to determine the position and orientation of the object.

6. The system according to claim 1, wherein the processing unit is configured to communicate with the at least one ultrasound transducers and to cause the ultrasound transducers to emit the initial ultrasound signals in a sequential manner.

7. The system according to claim 1, wherein each bubble has a diameter comprised between 20 µm and 1 mm.

8. The system according to claim 1, wherein each ultrasound transducer is configured to be fixed on the outside of a skull of a subject.

9. The system according to claim 1, wherein each ultrasound transducer is configured to be positioned in a hole made in the outer layers of a skull of a subject.

10. The system according to claim 1, comprising three bubbles configured to be distributed on the object without being aligned.

11. The system according to claim 1, comprising a registration module configured to match the coordinates of each point of the localization data generated by the processing unit with the coordinates of corresponding images on a reference image obtained with a medical imaging system, using image registration algorithms.

12. The system according to claim 1, wherein the processing unit is configured to use super-resolution processing to localize the object, said object being smaller than a wavelength of the emitted initial ultrasound signals.

13. The system according to claim 1, wherein the envelope of each bubble is made of a polymer.

14. The system according to claim 1, wherein the object is a microrobot.

15. The system according to claim 1, wherein the viscoelastic medium is an organ of a subject.

16. The system according to claim 1, wherein the hermetic envelope of each bubble has a thickness of less than 100 µm.

17. A method for real-time localization of a millimetric or submillimetric object in a viscoelastic medium based on an acoustic resonance of at least two distinct bubbles in the viscoelastic medium base, wherein at least two bubbles attached to said object, each bubble comprising a hermetic envelope filled with a gas, each bubble being configured to be either structurally anchored on the object or assembled with the object by means of at least one fastening element, the method comprising steps of:
by means of least one ultrasound transducer, producing emitted initial ultrasound signals at a given frequency and detecting deflected ultrasound signals deflected at the surface of the at least two distinct bubbles; and
by means of a processing unit in communication with the at least one ultra sound transducer, generating localization data of the object from localization data of the at least two distinct bubbles based on the deflected ultrasound signals detected by the at least one ultrasound transducer, wherein the at least two distinct bubbles are attached to the object in such a way that the localization of the at least two distinct bubbles enables the processing unit to determine a position and an orientation of the object.

18. The method according to claim 17, the method using at least three ultrasound transducers and comprising steps of:
producing emitted initial ultrasound pulses by means of the at least three ultrasound transducers in a sequential manner and detecting deflected ultrasound signals deflected at the surface of the at least two distinct bubbles by means of the at least three ultrasound transducers; and
generating the localization data of the object from localization data of the at least two distinct bubbles based on the deflected ultrasound signals detected by the at least three ultrasound transducers.

19. The method according to claim 17, wherein the object is a microrobot.

20. The method according to claim 17, wherein the viscoelastic medium is an organ of a subject.

* * * * *